Dec. 6, 1960 E. S. BOERNER Plant Pat. 1,995
CHRYSANTHEMUM PLANT
Filed Feb. 26, 1960
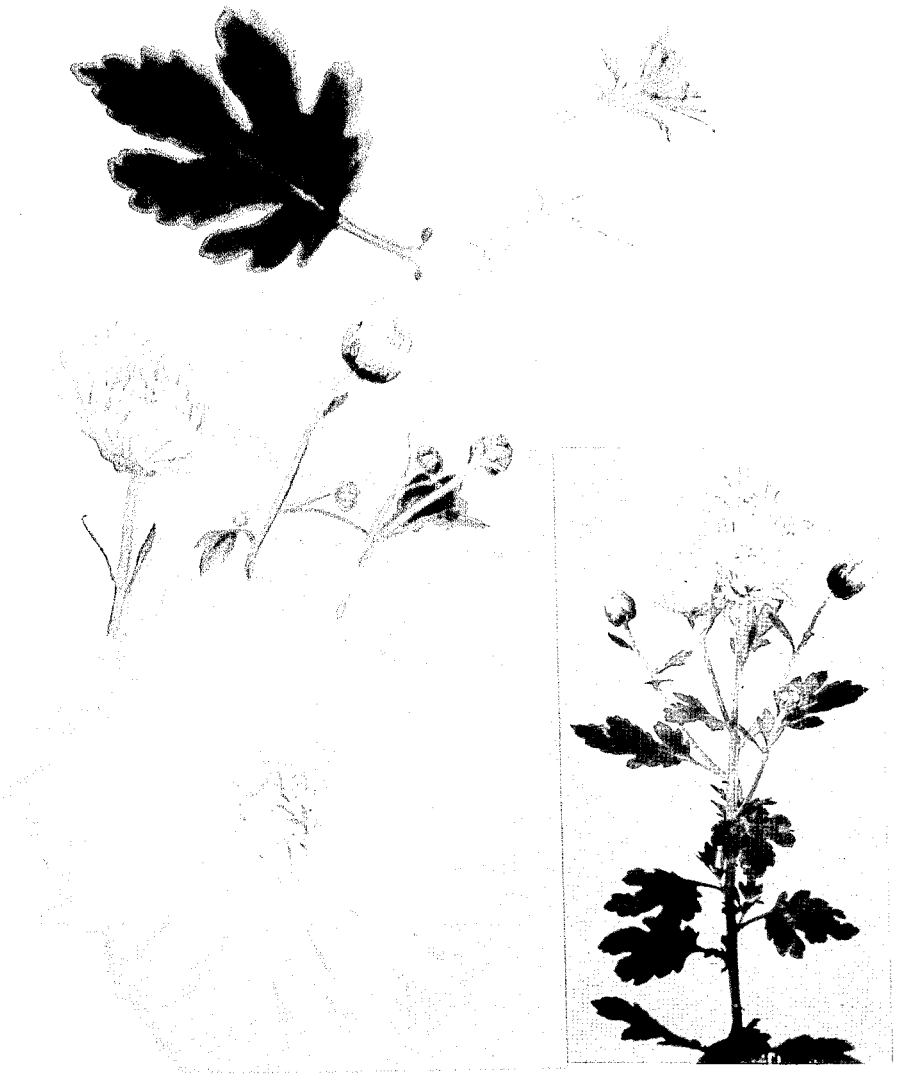
Inventor.
E. S. Boerner
By: Robb & Robb
Attorneys.

United States Patent Office

Plant Pat. 1,995
Patented Dec. 6, 1960

1,995

CHRYSANTHEMUM PLANT

Eugene S. Boerner, Newark, N.Y., assignor to Jackson & Perkins Company, Newark, N.Y., a corporation of New York Filed Feb. 26, 1960, Ser. No. 11,393

1 Claim. (Cl. 47—60)

The present invention relates to a new and distinct variety of chrysanthemum plant of the decorative flat type, which was originated by me by crossing an unnamed and unpatented seedling derived from a cross of "Flicker" (Plant Patent No. 1,465) × "Thrush" (Plant Patent No. 1,168) with the variety "Seagull" (Plant Patent No. 1,130).

The primary objective of this breeding was to obtain a new chrysanthemum variety having the plant habit, stem characteristics and vigor of the unnamed seedling parent, combined with the earliness and flower size of the flowers of the parent variety "Seagull." This objective was substantially achieved, as evidenced by the following characteristics which are outstanding in the new variety and which distinguish it from its parents, as well as from all other varieties of which I am aware:

(1) A vigorous plant habit, with stiff stems;
(2) Large flower size;
(3) A decorative and flat flower form; and
(4) A distinctive Apricot Yellow, lightly overcast with Empire Yellow, general color tonality of the flowers.

Asexual reproduction of the new variety by both top cuttings and underground runners, as performed at Newark, New York, shows that the foregoing characteristics and distinctions come true to form and are established and transmitted through succeeding propagations.

The accompanying drawing shows typical specimens of the vegetative growth and flowers of my new chrysanthemum variety in different stages of development and as depicted in color as nearly true as it is reasonably possible to make the same in a color illustration of this character, as well as a typical specimen plant which is depicted in black-and-white for the purpose of illustrating the form and habit of growth of the plant.

The following is a detailed description of the new variety, with color terminology in accordance with Ridgway's Color Standards and Nomenclature, as based upon observations made from specimens grown outdoors at Newark, New York, near mid-morning during the middle of the month of October:

Parentage: Seedling.
*Seed parent.*—An unnamed seedling derived from a cross of "Flicker" × "Thrust."
*Pollen Parent.*—"Seagull."

Classification: Decorative; flat.
Growth: Tall (attains height of from 30 to 36"); healthy.
Cold resistance: Plants are winter hardy in northern New York; flowers show slight frost-burn from early frosts.
Blooming period: In the Newark, New York, climatic area, average date of start of bloom is about the end of September, with blooms continuing until frost.

*Flower*

Bud:
*Color.*—When sepals first divide—Citron Yellow, Plate 16. When petals begin to unfurl—Deep Chrome, Plate 3. When half-blown: inside of petals—Cadmium Yellow, Plate 3; outside of petals—Deep Chrome, Plate 3, lightly overcast with Pinard Yellow, Plate 4 on the upper half of the petals.
*Peduncle.*—Color — Absinthe Green, Plate 31. Strength—strong.

Blooms:
*Size.*—5½".
*Stem.*—Strong.
*Form.*—Decorative; flat.
*Petalage.*—Double.
*Color.*—Center of flower—Light Cadmium, Plate 4, lightly overcast with Empire Yellow, Plate 4. Outer petals—Pale Lemon Yellow, Plate 4, lightly overcast with Empire Yellow, Plate 4. Base of petals—Pale Green-Yellow, Plate 5. Inside of petals—Apricot Yellow, Plate 4, lightly overcast with Empire Yellow, Plate 4. Reverse of petals—Pinard Yellow, Plate 4.
*Petals.*—Texture—soft. Form—long; flat.
*Fragrance.*—Characteristic chrysanthemum.

*Plant*

Form: Upright; stiff.
Growth: Vigorous.
Foliage:
*Size.*—Medium.
*Quantity.*—Normal.
*Color.*—Upper side—Forest Green, Plate 17. Under side—Light Bice Green, Plate 17.
*Texture.*—Stiff.

I claim:

A new and distinct variety of chrysanthemum plant of the decorative, flat class, substantially as herein shown and described, characterized particularly as to novelty by the unique combination of a vigorous and stiff-stemmed plant habit, large flower size, a decorative flat flower form, and a distinctive Apricot Yellow, lightly overcast with Empire Yellow general color tonality of the flowers.

No references cited.